US009326861B2

(12) United States Patent
Iott et al.

(10) Patent No.: US 9,326,861 B2
(45) Date of Patent: May 3, 2016

(54) STABILIZING JOINTS

(75) Inventors: Andrew Iott, Villanova, PA (US); Jody L. Seifert, Birdsboro, PA (US); David C. Paul, Phoenixville, PA (US); Mark Adams, Downingtown, PA (US); Kevin Gahman, Douglassville, PA (US); Chad Glerum, Pennsburg, PA (US); Daniel Davenport, Collegeville, PA (US); Victoria Alexander, Royersford, PA (US)

(73) Assignee: GLOBUS MEDICAL, INC., Audubon, PA (US)

(*) Notice: Subject to any disclaimer, the term of this patent is extended or adjusted under 35 U.S.C. 154(b) by 55 days.

(21) Appl. No.: 13/566,899

(22) Filed: Aug. 3, 2012

(65) Prior Publication Data

US 2014/0039623 A1   Feb. 6, 2014

(51) Int. Cl.
*A61F 2/44* (2006.01)
*A61F 2/30* (2006.01)

(52) U.S. Cl.
CPC ............. *A61F 2/30744* (2013.01); *A61F 2/447* (2013.01); *A61F 2/4455* (2013.01); *A61F 2002/305* (2013.01); *A61F 2002/3008* (2013.01); *A61F 2002/30331* (2013.01); *A61F 2002/30387* (2013.01); *A61F 2002/30388* (2013.01); *A61F 2002/30433* (2013.01); *A61F 2002/30438* (2013.01); *A61F 2002/30448* (2013.01); *A61F 2002/30492* (2013.01); *A61F 2002/30509* (2013.01); *A61F 2002/30538* (2013.01); *A61F 2002/30578* (2013.01); *A61F 2002/30714* (2013.01); *A61F 2002/30787* (2013.01); *A61F 2002/30836* (2013.01); *A61F 2002/4475* (2013.01); *A61F 2310/00023* (2013.01)

(58) Field of Classification Search
CPC .................... A61F 2/4455; A61F 2310/00023
USPC ........................................................ 623/17.16
See application file for complete search history.

(56) References Cited

U.S. PATENT DOCUMENTS

| 1,673,630 | A | 6/1928 | Madge |
| 4,349,921 | A | 9/1982 | Kuntz |

(Continued)

FOREIGN PATENT DOCUMENTS

| FR | 2727003 A1 | 5/1996 |
| WO | 9723175 A1 | 7/1997 |

(Continued)

OTHER PUBLICATIONS

Guidance Document: Intervertebral Body Fusion Device, U.S. Dept of Health and Human Services, Food and Drug Administration (Jun. 12, 2007).
M. Spruit et al., The in vitro stabilizing effect of polyetheretherketone cages versus a titanium cage of similar design for anterior lumbar interbody fusion, 14(8) Eur. Spine J. 752, 752-758 (2005).

(Continued)

*Primary Examiner* — Ellen C Hammond (57) ABSTRACT

An intervertebral spacer and stabilization implant includes a plate having sockets configured for retaining a fastener passable through the socket and into an adjacent vertebral body. One or more connecting projections extend from a side of the plate, to mate with projections extending from a spacer body. A plurality of teeth project from at least one of the upper or lower surfaces of the spacer body, and a chamber is formed through the spacer body to enable bone fusion between the vertebrae. The combined plate and spacer may be inserted to lie completely within the intervertebral space, or a portion of the plate may overlie a vertebral body.

16 Claims, 7 Drawing Sheets

(56) References Cited

U.S. PATENT DOCUMENTS

| | | |
|---|---|---|
| 4,599,086 A | 7/1986 | Doty |
| 4,743,256 A | 5/1988 | Brantigan |
| 4,834,757 A | 5/1989 | Brantigan |
| 4,904,261 A | 2/1990 | Dove et al. |
| 4,917,704 A | 4/1990 | Frey |
| 4,955,908 A | 9/1990 | Frey |
| 5,002,576 A | 3/1991 | Fuhrmann et al. |
| 5,364,399 A | 11/1994 | Lowery et al. |
| 5,397,364 A | 3/1995 | Kozak et al. |
| 5,458,641 A | 10/1995 | Jimenez |
| 5,514,180 A | 5/1996 | Heggeness |
| 5,549,612 A | 8/1996 | Yapp et al. |
| 5,645,596 A | 7/1997 | Kim et al. |
| 5,861,041 A | 1/1999 | Tienboon |
| 5,888,223 A | 3/1999 | Bray, Jr. |
| 6,045,579 A | 4/2000 | Hochshuler |
| 6,066,175 A | 5/2000 | Henderson et al. |
| 6,113,638 A * | 9/2000 | Williams et al. ............ 128/898 |
| 6,146,421 A | 11/2000 | Gordon |
| 6,156,037 A | 12/2000 | LeHuec et al. |
| 6,200,347 B1 | 3/2001 | Anderson et al. |
| 6,206,922 B1 | 3/2001 | Zdeblick et al. |
| 6,231,610 B1 | 5/2001 | Geisler |
| 6,235,059 B1 | 5/2001 | Benezech |
| 6,258,089 B1 | 7/2001 | Campbell et al. |
| 6,342,074 B1 | 1/2002 | Simpson |
| 6,364,880 B1 | 4/2002 | Michelson |
| 6,383,186 B1 | 5/2002 | Michelson |
| 6,425,920 B1 | 7/2002 | Hamada |
| 6,432,106 B1 | 8/2002 | Fraser |
| 6,471,724 B2 | 10/2002 | Zdeblick |
| 6,482,233 B1 | 11/2002 | Aebi |
| 6,520,993 B2 | 2/2003 | James |
| 6,540,785 B1 | 4/2003 | Gill et al. |
| 6,558,387 B2 | 5/2003 | Errico |
| 6,558,423 B1 | 5/2003 | Michelson |
| 6,558,424 B2 | 5/2003 | Thalgott |
| 6,562,073 B2 | 5/2003 | Foley |
| 6,629,998 B1 | 10/2003 | Lin |
| 6,666,889 B1 | 12/2003 | Commarmond |
| 6,682,563 B2 | 1/2004 | Scharf |
| 6,709,458 B2 | 3/2004 | Michelson |
| 6,730,127 B2 | 5/2004 | Michelson |
| 6,740,118 B2 | 5/2004 | Eisermann et al. |
| 6,793,658 B2 | 9/2004 | Lehuec |
| 6,805,714 B2 | 10/2004 | Sutcliffe |
| 6,827,740 B1 | 12/2004 | Michelson |
| 6,835,206 B2 | 12/2004 | Jackson |
| 6,849,093 B2 | 2/2005 | Michelson |
| 6,887,272 B2 | 5/2005 | Shinomiya |
| 6,899,735 B2 | 5/2005 | Coates et al. |
| 6,972,019 B2 | 12/2005 | Michelson |
| 7,001,432 B2 | 2/2006 | Keller et al. |
| 7,025,787 B2 | 4/2006 | Bryan et al. |
| 7,044,972 B2 | 5/2006 | Mathys, Jr. |
| 7,137,997 B2 | 11/2006 | Paul |
| 7,147,665 B1 | 12/2006 | Bryan et al. |
| 7,153,325 B2 | 12/2006 | Kim et al. |
| 7,163,561 B2 | 1/2007 | Michelson |
| 7,172,627 B2 | 2/2007 | Fiere et al. |
| 7,192,447 B2 | 3/2007 | Rhoda |
| 7,232,464 B2 | 6/2007 | Mathieu et al. |
| 7,238,203 B2 | 7/2007 | Bagga et al. |
| 7,276,082 B2 | 10/2007 | Zdeblick et al. |
| 7,309,357 B2 | 12/2007 | Kim |
| 7,320,708 B1 | 1/2008 | Bernstein |
| 7,594,931 B2 | 9/2009 | Louis et al. |
| 7,618,456 B2 | 11/2009 | Mathieu et al. |
| 7,771,475 B2 | 8/2010 | Michelson |
| 7,794,502 B2 | 9/2010 | Michelson |
| 7,846,207 B2 * | 12/2010 | Lechmann et al. ......... 623/17.11 |
| 7,850,731 B2 * | 12/2010 | Brittan et al. ............ 623/17.11 |
| 7,862,616 B2 * | 1/2011 | Lechmann et al. ......... 623/17.11 |
| 7,875,076 B2 | 1/2011 | Mathieu et al. |
| 7,972,381 B2 | 7/2011 | Michelson |
| 8,100,976 B2 | 1/2012 | Bray et al. |
| 8,105,383 B2 | 1/2012 | Michelson |
| 8,114,162 B1 | 2/2012 | Bradley |
| 8,137,405 B2 | 3/2012 | Kostuik et al. |
| 8,216,312 B2 | 7/2012 | Gray |
| 8,268,000 B2 * | 9/2012 | Waugh et al. ............ 623/17.16 |
| 8,323,343 B2 | 12/2012 | Michelson |
| 8,328,872 B2 * | 12/2012 | Duffield et al. ............ 623/17.16 |
| 8,343,222 B2 | 1/2013 | Cope |
| 8,425,607 B2 | 4/2013 | Waugh et al. |
| 8,439,977 B2 | 5/2013 | Kostuik et al. |
| 8,540,774 B2 * | 9/2013 | Kueenzi et al. ............ 623/17.16 |
| 8,641,765 B2 * | 2/2014 | Muhanna .................. 623/17.16 |
| 8,641,766 B2 * | 2/2014 | Donner et al. ............ 623/17.16 |
| 8,641,768 B2 * | 2/2014 | Duffield et al. ............ 623/17.16 |
| 8,709,083 B2 * | 4/2014 | Duffield et al. ............ 623/17.16 |
| 8,709,085 B2 * | 4/2014 | Lechmann et al. ........ 623/17.16 |
| 8,715,354 B2 * | 5/2014 | Lechmann et al. ........ 623/17.16 |
| 2001/0005796 A1 | 6/2001 | Zdeblick |
| 2001/0034553 A1 | 10/2001 | Michelson |
| 2002/0004683 A1 | 1/2002 | Michelson |
| 2002/0010511 A1 | 1/2002 | Michelson |
| 2002/0016595 A1 | 2/2002 | Michelson |
| 2002/0082597 A1 | 6/2002 | Fraser |
| 2002/0138146 A1 | 9/2002 | Jackson |
| 2002/0143399 A1 | 10/2002 | Sutcliffe |
| 2002/0147450 A1 | 10/2002 | Lehuec |
| 2003/0045939 A1 | 3/2003 | Casutt |
| 2003/0105528 A1 | 6/2003 | Shimp et al. |
| 2003/0125739 A1 | 7/2003 | Bagga et al. |
| 2003/0167091 A1 | 9/2003 | Scharf |
| 2003/0181981 A1 | 9/2003 | Lemaire |
| 2004/0078078 A1 | 4/2004 | Shepard |
| 2004/0082998 A1 | 4/2004 | Shinomiya |
| 2004/0082999 A1 | 4/2004 | Mathys, Jr. |
| 2004/0117018 A1 | 6/2004 | Michelson |
| 2004/0143270 A1 | 7/2004 | Zucherman et al. |
| 2004/0143332 A1 | 7/2004 | Krueger et al. |
| 2004/0176853 A1 | 9/2004 | Sennett et al. |
| 2005/0055098 A1 | 3/2005 | Zdeblick et al. |
| 2005/0065607 A1 | 3/2005 | Gross |
| 2005/0149192 A1 | 7/2005 | Zucherman et al. |
| 2005/0149193 A1 | 7/2005 | Zucherman et al. |
| 2005/0159819 A1 | 7/2005 | McCormack et al. |
| 2005/0171607 A1 | 8/2005 | Michelson |
| 2005/0177236 A1 | 8/2005 | Mathieu et al. |
| 2005/0187625 A1 | 8/2005 | Wolek et al. |
| 2005/0240267 A1 | 10/2005 | Randall et al. |
| 2005/0240271 A1 | 10/2005 | Zubok et al. |
| 2005/0256574 A1 | 11/2005 | Paul et al. |
| 2006/0085071 A1 | 4/2006 | Lechmann et al. |
| 2006/0129240 A1 | 6/2006 | Lessar et al. |
| 2006/0217809 A1 | 9/2006 | Albert et al. |
| 2007/0088441 A1 | 4/2007 | Duggal et al. |
| 2007/0106388 A1 | 5/2007 | Michelson |
| 2007/0123987 A1 | 5/2007 | Bernstein |
| 2007/0135923 A1 | 6/2007 | Peterman et al. |
| 2007/0162130 A1 | 7/2007 | Rashbaum et al. |
| 2007/0168032 A1 | 7/2007 | Muhanna et al. |
| 2007/0225806 A1 | 9/2007 | Squires et al. |
| 2007/0225810 A1 | 9/2007 | Colleran et al. |
| 2007/0225812 A1 | 9/2007 | Gill |
| 2007/0233253 A1 | 10/2007 | Bray et al. |
| 2007/0250167 A1 | 10/2007 | Bray et al. |
| 2007/0270961 A1 | 11/2007 | Ferguson |
| 2008/0051890 A1 | 2/2008 | Waugh et al. |
| 2008/0051907 A1 | 2/2008 | Marik |
| 2008/0133013 A1 | 6/2008 | Duggal et al. |
| 2009/0076608 A1 | 3/2009 | Gordon et al. |
| 2009/0105830 A1 * | 4/2009 | Jones et al. ............... 623/17.16 |
| 2009/0105831 A1 * | 4/2009 | Jones et al. ............... 623/17.16 |
| 2009/0210062 A1 * | 8/2009 | Thalgott et al. ............ 623/17.16 |
| 2010/0057206 A1 * | 3/2010 | Duffield et al. ............ 623/17.16 |
| 2010/0145460 A1 * | 6/2010 | McDonough et al. ..... 623/17.16 |
| 2011/0087327 A1 * | 4/2011 | Lechmann et al. ........ 623/17.11 |
| 2011/0166658 A1 | 7/2011 | Garber et al. |
| 2011/0251689 A1 * | 10/2011 | Seifert et al. ............... 623/17.16 |
| 2012/0245690 A1 | 9/2012 | Cowan, Jr. et al. |

(56) References Cited

U.S. PATENT DOCUMENTS

| | | |
|---|---|---|
| 2013/0110247 A1 | 5/2013 | Doran et al. |
| 2014/0012380 A1 | 1/2014 | Laurence et al. |
| 2014/0039623 A1 | 2/2014 | Iott et al. |

FOREIGN PATENT DOCUMENTS

| | | |
|---|---|---|
| WO | 9963914 A1 | 12/1999 |
| WO | 2005007040 A1 | 1/2005 |
| WO | 2007098288 A2 | 8/2007 |
| WO | 2008014258 A2 | 1/2008 |

OTHER PUBLICATIONS

P. Schleicher et al., Biomechanical comparison of two different concepts for stand alone anterior lumbar interbody fusion, 17(12) Eur. Spine J. 1757, 1757-1765 (2008).

P.W. Pavlov et al., Anterior lumbar interbody fusion with threaded fusion cages and autologous bone grafts, 9 Eur. Spine J. 224, 224-229 (2000).

Synthes' SynFix Technique Guide device ("SynFix Technique Guide").

* cited by examiner

STABILIZING JOINTS

FIELD OF THE INVENTION

The invention relates to stabilizing joints using a spacer, and more particularly stabilizing the spine using an intervertebral spacer and plate secured by fasteners.

BACKGROUND OF THE INVENTION

Bones and bony structures are susceptible to a variety of weaknesses that can affect their ability to provide support and structure. Weaknesses in bony structures have numerous potential causes, including degenerative diseases, tumors, fractures, and dislocations. Intervertebral discs in the spinal column degenerate more rapidly as people grow older. This results in a loss of water content, and ultimately a loss of height. As a result, the nerves exiting from the spinal canal 132 become compressed and pinched, which causes pain, among other neurological deficits.

In some cases, the spinal column requires additional support in order to address such weaknesses and compression. One technique for providing support is to insert a spacer between adjacent vertebrae, to compensate for a failure of the structures whose role it is to separate and help align adjacent vertebrae.

Preparation of the intervertebral disc space includes forming an opening in the annulus fibrosus, and clearing at least a portion of the nucleus pulposus to make room for the spacer. The spacer is inserted into the space, and may be attached to the adjacent bony structures using fasteners, such as bone screws. In some cases, a bone growth material may be placed together with the spacer to promote fusion of the adjacent vertebrae.

SUMMARY OF THE INVENTION

In accordance with an embodiment of the disclosure, a device for separating and stabilizing first and second adjacent vertebrae together defining an intervertebral space between them, comprises a plate including a plurality of sockets each configured for retaining a fastener passable through the socket and into the first or second vertebral body, and one or more connecting projections extending from a side of the plate; a spacer body sized and dimensioned to be contained completely within the intervertebral space and including an upper surface engageable with the first vertebral body, a lower surface engageable with the second vertebral body, a plurality of teeth projecting from at least one of the upper or lower surface, a chamber formed by an opening extending between the upper and lower surfaces, and one or more connecting projections mateable with the one or more connecting projections of the plate to thereby securely mutually connect the plate and the spacer body.

In various embodiments thereof, the plate is sized and dimensioned to be contained completely within the intervertebral space; the plate is sized and dimensioned to extend outside of the intervertebral space; a fastener extends between the connecting projections of the plate and the connecting projections of the body; the projections of the body form a recess into which a connecting projection of the plate extends; and a connecting projection of the plate includes a plurality of teeth or an edge configured to engage a vertebral body.

In other embodiments thereof, a fastener passed through the socket and into the first or second vertebral body lies partially within a channel formed in the upper or lower surface; no portion of a fastener passed through the socket and into the first or second vertebral body extends outside the intervertebral space; the device further includes a recess formed in at least one of the plate or body for engaging a surgical instrument for maneuvering the device; the device further includes a blocking cam screw configured to block movement of a fastener passed through one of the sockets in a direction of passing out of one of the sockets; and the blocking cam screw includes a blocking head having a cam profile including a fastener access portion and a fastener blocking portion.

In yet further embodiments thereof, the plurality of sockets include an odd number of sockets, a relatively unequal number of sockets thereby disposed on opposing sides of the device; the plate further includes at least one edge extending therefrom and configured to enter a vertebral body when the device is implanted between adjacent vertebrae; the edge is aligned in an anterior-posterior direction when the device is implanted, the edge thereby configured to resist a lateral movement of the device; the chamber is configured to admit the introduction of bone growth material, and to permit the growth of bone from the adjacent vertebrae, into the chamber and through the device; and the device is configured to be inserted from an anterior approach to the intervertebral space, after the removal of body tissue from the intervertebral space.

In further embodiments thereof, the plate and body connecting projections are mutually secured in engagement by at least one threaded fastener; the plate is pivotally connected to the body whereby rotation of the plate with respect to the body operates to engage or disengage mating connecting projections of the plate and body; the plate is formed in at least two portions, the plate connecting projections formed upon each of the at least two portions; the plate and body connecting projections mutually form a dovetail connection; and the plate and body connecting projections maintained in engagement by a biasing element.

In an embodiment thereof, a twist-lock connection is formed between the body and the plate, one of the plate and body forming a projecting connector portion and the other of the plate and body forming a recessed connector portion, the projecting connector portion including a flange and the recessed connector portion including a channel and a stop surface.

In further embodiments thereof, the plate and body connecting projections are maintained in engagement by a threaded fastener passable from the plate into the body; and the threaded fastener further including a blocking cam profile configured to admit a fastener into one of the plurality of sockets in a first position, and block passage of the fastener out of the one of the plurality of sockets in a second position; and the device is configured to be inserted from a lateral approach to the intervertebral space, after the removal of body tissue from the intervertebral space.

In another embodiment, a device for separating and stabilizing first and second adjacent vertebrae together defining an intervertebral space between them, comprises a plate including a plurality of sockets each configured for retaining a fastener passable through the socket and into the first or second vertebral body, and one or more connecting projections extending from a side of the plate; a spacer body sized and dimensioned to be contained completely within the intervertebral space and including an upper surface engageable with the first vertebral body, a lower surface engageable with the second vertebral body, a plurality of teeth projecting from at least one of the upper or lower surface, a chamber formed by an opening extending between the upper and lower surfaces, and one or more connecting projections mateable with the one or more connecting projections of the plate to thereby securely mutually connect the plate and the spacer body; and a fastener passable through the plate and connectable with the body, the fastener configured to maintain a mateable engagement between the plate and body connecting projections, the fastener further including a blocking cam profile configured to admit a fastener into one of the plurality of sockets in a first position, and block passage of the fastener out of the one of the plurality of sockets in a second position.

In a further embodiment, a device for separating and stabilizing first and second adjacent vertebrae together defining an intervertebral space between them, comprises a plate including a plurality of sockets each configured for retaining a fastener passable through the socket and into the first or second vertebral body, the plurality of sockets extending outside the intervertebral space, and one or more connecting projections extending from a side of the plate; a spacer body sized and dimensioned to be contained completely within the intervertebral space and including an upper surface engageable with the first vertebral body, a lower surface engageable with the second vertebral body, a plurality of teeth projecting from at least one of the upper or lower surface, a chamber formed by an opening extending between the upper and lower surfaces, and one or more connecting projections mateable with the one or more connecting projections of the plate to thereby securely mutually connect the plate and the spacer body; wherein the plate and body, when mateably connected by the plate and body connecting projections, is configured to be inserted into the intervertebral space from a substantially lateral approach.

In an embodiment thereof, the body is configured to overlie cortical bone of the adjacent vertebral bodies along opposite sides of each adjacent vertebral body.

BRIEF DESCRIPTION OF THE DRAWINGS

A more complete understanding of the present invention, and the attendant advantages and features thereof, will be more readily understood by reference to the following detailed description when considered in conjunction with the accompanying drawings, in which:

FIG. 19 is a side view of the device of FIG. 16;

FIG. 21 is a top view of the device of FIG. 20;

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

In accordance with the disclosure, a solution to the problems of weaknesses in the vertebral column, and a loss of spacing between vertebrae, is to insert a spacer in place of the disc, to restore lost height, and to promote adjacent vertebral bodies to fuse permanently to maintain this height restoration. Additional fixation may also be needed to stabilize the spinal segment, typically provided by a plate that rests on an anterior aspect of the vertebral body.

Figures 1, 2, 3, 4, 5:
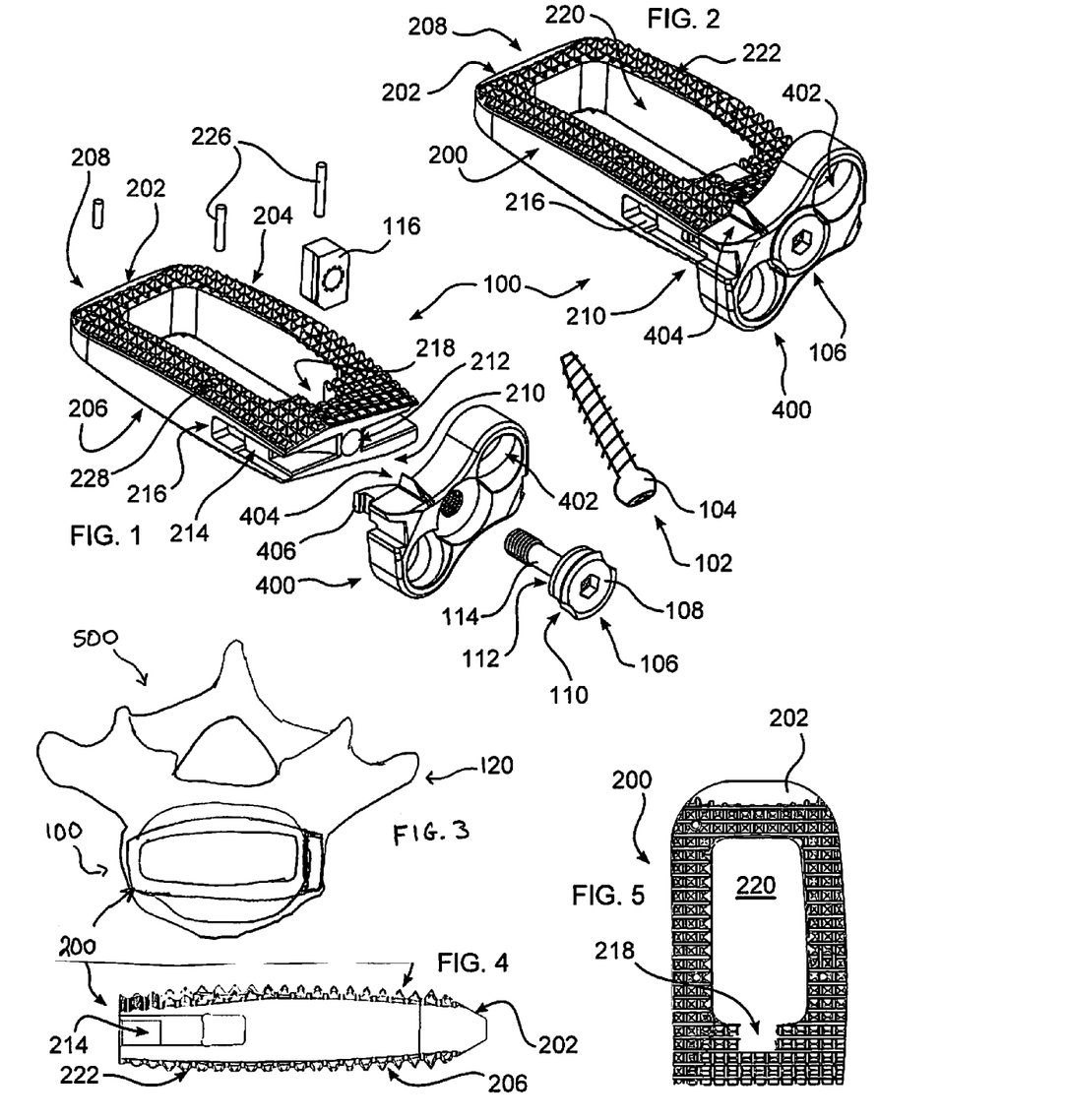
FIG. 1 is an illustration in perspective view of a spacing and stabilization device of the disclosure, including a combined spacer and plate, the device adapted for insertion within the joint space from a lateral approach.
FIG. 2 is a another view of the device of FIG. 1.
FIG. 3 is a superior view of the device of FIG. 1, implanted in the intervertebral space.
FIG. 4 is a side view of the spacer body of FIG. 1.
FIG. 5 is a top view of the spacer body of FIG. 1.

With reference to FIG. 1, device 100 is an interbody bone fusion device intended for use in patients with degenerative disc disease (DDD) at, typically, one or two contiguous levels of the spine, although a greater number of levels are possible. Device 100 is advantageous, for example, in patients who have up to Grade 1 spondylolisthesis or retrolisthesis at the spinal levels for which device 100 is being considered. Device 100 is advantageously filled with bone graft material, advantageously autogenous material.

Device 100 is formed from two separable components, a spacer body 200, and a plate 400. Body 200 is formed to have an elongated shape inserted from a lateral, anterio-lateral, or posterio-lateral approach to the spine. A leading end 208 and a trailing end 210 are defined with respect to a direction of insertion of device 100. In one embodiment, a taper or chamfer 202 is provided along leading end 208, which operates to distract the vertebral bodies during insertion, and to ease insertion. Teeth 222, disposed on superior and inferior aspects of the spacer body 200, help prevent migration of the spacer. In both aspects, the tooth base defines a contact plane for the adjacent vertebral body. While certain embodiments illustrated herein do not show teeth, it should be understood that teeth may be provided upon a surface of any of the embodiments.

An advantage of a lateral approach is the enablement of safely overlying cortical bone on opposite sides of the vertebral bodies with the spacer body, as the spinal canal is not approached in this orientation. In this manner, a load placed upon the spacer body is distributed to the strongest portions of the vertebrae. In this configuration, the spacer body is accordingly sized to be substantially longer in a lateral dimension than in its width, or anterior-posterior (A/P) dimension.

Figure 18:
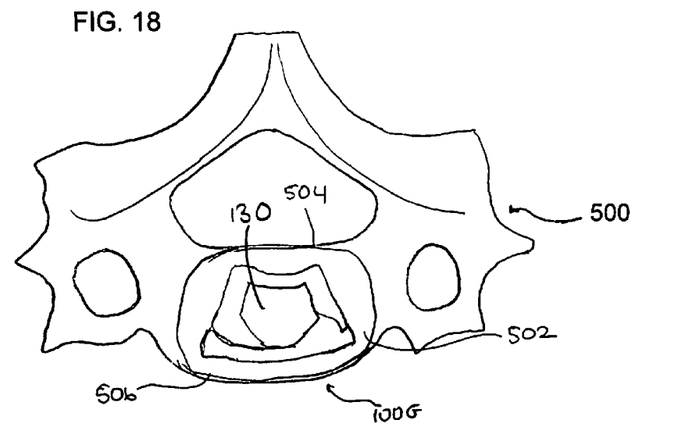
FIG. 18 is a superior view of the device of FIG. 16 implanted within an intervertebral space.
Figure 20:
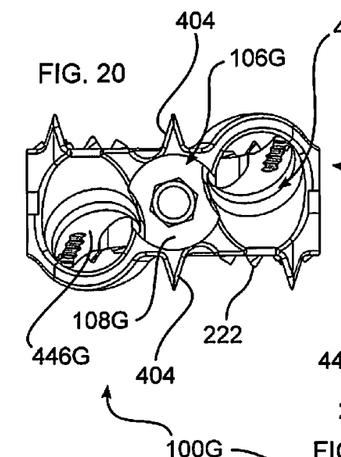
FIG. 20 is a front view of the device of FIG. 16.
Figures 24, 25:
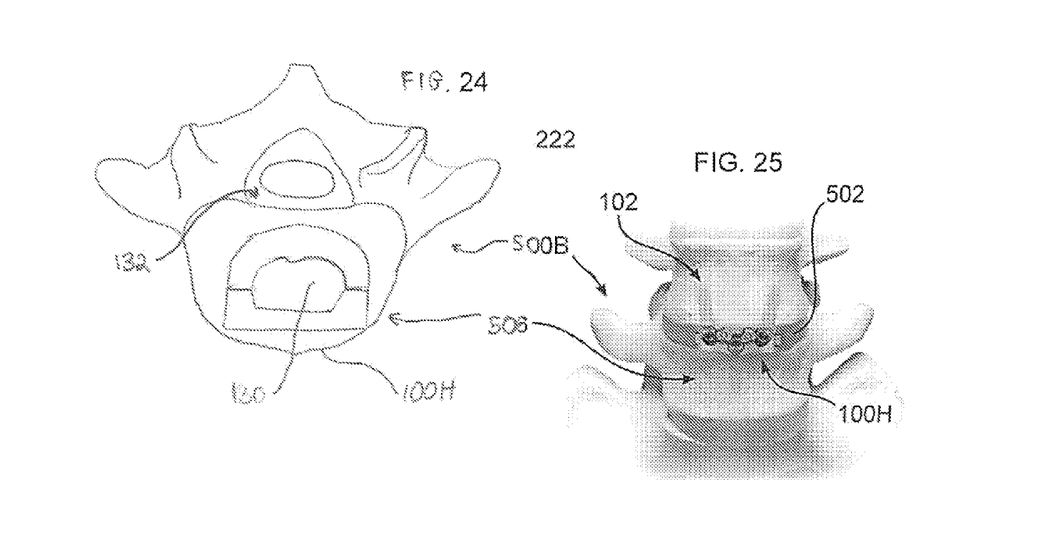
FIG. 24 is a superior view of the device of FIG. 23 implanted within the intervertebral space.
FIG. 25 is an anterior view of the device of FIG. 23 implanted within the intervertebral space.
Figures 26, 27, 28:
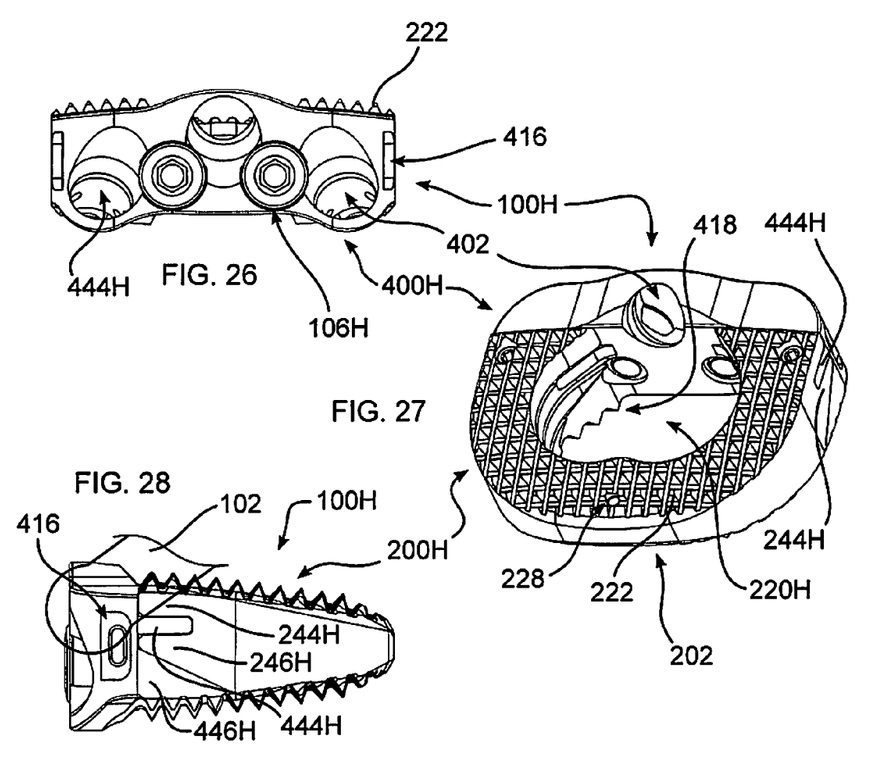
FIG. 26 is a front view of the device of FIG. 23.
FIG. 27 is a rear perspective view of the device of FIG. 23.
FIG. 28 is a side view of the device of FIG. 23.

An opening within body 200 creates an enclosed volume or chamber 220 into which an optimal quantity of bone graft material 130 (shown in FIGS. 18 and 24), such as autograft, allograft, xenograft, or artificial material may be packed. The bone graft material 130 may advantageously be combined with a bone growth material, such as insulin-like growth factors, transforming growth factor-beta, fibroblast growth factor, platelet-derived growth factor, and bone morphogenetic proteins. An ultimate goal of the use of such materials may be the growth for bone between vertebrae, resulting in a fusion and stabilization of the spinal column. It may be therapeutically advantageous to maintain some movement between adjacent vertebrae, in which case no materials are placed within chamber 220, or alternative, materials which do not foster bone growth between vertebrae.

A plurality of fasteners 102, advantageously titanium alloy screws, connect plate 400 with body tissue, for example cortical bone or cancellous bone of adjacent vertebrae. Fasteners 102 may be provided together with device 100 to ensure correct sizing, shape, biocompatibility, and strength. Fasteners 102 may advantageously be inserted at an angle with respect to a contact plane of spacer body 200, which contributes to optimal screw purchase into adjacent superior and inferior vertebral bodies. In an embodiment, fasteners 102 are polyaxial screws, and are positionable within sockets 402 within plate 400. For example, sockets 402 may likewise be polyaxial, or may dispose a fastener 102 at a specific angular orientation. Tortional stabilizers 404, advantagesouly having the form of knife edges, are advantageously provided to extend from plate 400 to contact body tissue.

In one embodiment, spacer body 200 is biconvex, and is provided in lordotic options in various degrees. More particularly, each of an upper surface 204 and a lower surface 206 form a convex shaped curved surface with respect to a longitudinal central axis of body 200. Body 200 may be lordotic in that a thickness of body 200 between upper and lower surfaces 204, 206 may be different at leading end 208 and trailing end 210, or even laterally, as therapeutically indicated. As such, body 200 may change an angular relative disposition of adjacent vertebrae to correct a misalignment of the vertebrae.

The spacer body 200 and or plate 400 is advantageously fabricated from a biocompatible polymeric material, including for example PEEK (polyether ether ketone), POM (polyoxymethylene), HDPE (high density polyethylene), PPSU (polyphenylsulfone), or acrylic. Alternatively, spacer body 200 and or plate 400 may be fabricated from a biocompatible metal, including for example titanium and titanium alloys, tantalum, cobalt-chromium alloy, or stainless steel. Other materials from which body 200 or plate 400 may be fabricated include zirconium alloys, oxidized zirconium, and ceramics or ceramic composites. In another embodiment, spacer body 200 and or plate 400 may be formed with biodegradable plastics, whereby the materials are intended to completely degrade after fusion has taken place. In one embodiment, for example, body 200 is fabricated from PEEK, and plate 400 is fabricated from titanium. It is advantageous for plates of the disclosure to be made from a stronger material, such as metal, because the bending forces acting upon the plate, which is rigidly connected between two bones, are significant. The spacer bodies of the disclosure are subjected to greater forces of compression, and less of bending, and therefore are advantageously formed of a softer material, including polymers. Some resilience, however, for either plates or bodies, may be advantageous, for example to reduce stresses upon the body, and to reduce the potential for damage or failure of the device.

In accordance with an embodiment of the disclosure, fasteners 102 are blocked from reversing from engagement with body tissue. In the embodiment of FIGS. 1-2, a blocking cam screw 106 is provided on plate 400 to secure head 104 of inserted fasteners 102, to prevent fasteners 102 from backing away from plate 400. Blocking cam screw 106 includes a blocking head 108 having a cam profile including a narrowed portion 110 which admits access to the fastener 102 head, and a widened portion 112 which blocks a fastener 102 head, for each fastener 102 to be secured. Fastener 102 is inserted into socket 402, moving past narrowed portion 110, after which blocking cam screw 106 is rotated to position widened portion 112 to abut or engage a lateral portion of head 104, thereby preventing a reverse movement of fastener 102. Blocking cam screw 106 may be press-fit or threadably engaged with plate 400 and or body 200. In the embodiment illustrated in FIGS. 1-2, a threaded shaft 114 passes through an aperture 212 in body 200. In an embodiment, body 200 is provided with mating threads. In the embodiment shown, a nut 116 is provided, for example a metallic nut, particularly if body 200 is polymeric, to provide additional reliability and holding strength. As illustrated, nut 116 may be received and or secured within a recess 218 in body 200, to reduce a likelihood of the loss of nut 116 during surgery, and to prevent displacement of nut 116 within the body if blocking cam screw 106 is loosened or disconnected therefrom. Plate 400 may additionally be threaded to prevent undesired separation of blocking cam screw 106 from plate 400.

In an embodiment, plate 400 is further secured in connection with body 200 through a mortise and tenon joint connection. In the example shown, a bridle joint connection is formed between a mortise 214 within body 200, and a tenon 406 extending from plate 400. One or more dowel pins or screws, not shown, may pass through mortise 214 and tenon 406 to further secure the connection. Mortise and tenon 214, 406 may further be shaped to form a tool aperture 216 engageable by a surgical instrument used to insert and manipulate device 100 with respect to the body. The relative position of mortise 214 and tenon 406 may be reversed, wherein body 200 forms tenon 406, and plate 400 forms mortise 214.

To enhance visualization during implantation, removal, and diagnosis, markers exhibiting high contrast relative to body tissue may be combined with device 100, including for example radiopaque markers 226 embedded within marker bores 228 within body 200. If device 100 is formed of a sufficiently radiopaque material, such discrete markers may not be needed. Markers 226 are positioned so that an orientation of device 100 may be determined from a location of markers 226 in a diagnostic image, even if no other portion of device 100 can be visualized.

Teeth 222, if present, extend from one or both of upper and lower surfaces 204, 206, and are shaped to pierce body tissue to secure device 100 in a desired location. Teeth 222 may be angled to facilitate insertion, and to reduce a likelihood of migration in a direction opposite or sideways relative to a direction of insertion, or migration further into the intervertebral space.

Plate 400 may be selected from a variety of plates 400 of varying size and dimensions, and may be connected to body 200 before or at the time of surgery, to form an optimal therapeutic fit for an individual patient. Alternatively, plate 400 may be replaced after surgery, for example during revision surgery, in response to an event such as bone degradation. Further, plates may be provided for either fixed or angular displacement of any of fastener 102.

The assembled plate 400 and body 200 may be sized and dimensioned either to position a portion of device 100 to protrude exterior to the disc space between adjacent vertebrae, or the entirety of device 100 may lie completely within the disc space. In one embodiment, all or a portion of plate 400 extends from or away from the disc space, body 200 lying substantially entirely within the disc space; in such an embodiment, sockets 402 may have a reduced diameter, for example. In another embodiment, a portion of plate 400 extends above and below the disc space allowing a portion of the plate or bone screw to engage a side surface of the vertebral body.

Sockets 402 in plate 400 are advantageously displaced relative to upper and or lower surface 204, 206 of body 200, whereby the fasteners 102 are securely captured, yet at least a portion of fastener 102 lies above a surface plane of the spacer body 200. Accordingly, the structural strength of the body 200, as well as the area of the supporting surface of body 200, are favored by the removal of less spacer body material than a non-displaced aperture. Advantageously, the upper or lower surface 204, 206 are not relieved or do not otherwise form channels through which a portion of fasteners 102 must pass, thereby maintaining the greatest amount of strength and surface area for separating bones of the joint.

Device 100 is advantageously implanted from a lateral approach, transverse to an anterior-posterior (AP) orientation. As may be seen in FIG. 3, a vertebral body 500 of a target vertebra 500 is wider along a lateral axis than an AP axis. Accordingly, device 100 has corresponding dimensions. More particularly, average adult vertebral bodies have been found to vary between 29.29 and 35.74 mm in the AP direction (indicated by the dashed blue arrow and the indicia "AP"), and device 100 therefore has an implanted width along this axis that is substantially less than the smallest dimension of 29.29 mm. However, in order to provide a more stable support to adjacent vertebrae, device 100 has a length in the lateral direction which is selected to be sufficiently long to extend substantially a full width of the vertebrae, to contact cortical bone at each end of the device. Accordingly, the shortest length of body 200 is advantageously 35 mm, increasing to a maximum length of 40 mm. With such dimensions, device 100 should not be implanted to extend in an AP orientation, due to actual or potential interference with the spinal cord within the vertebral foramen. Notwithstanding the foregoing, variations in human or animal physiology, or other considerations, may favor variation from these considerations when therapeutically indicated.

Figures 6, 7, 8:
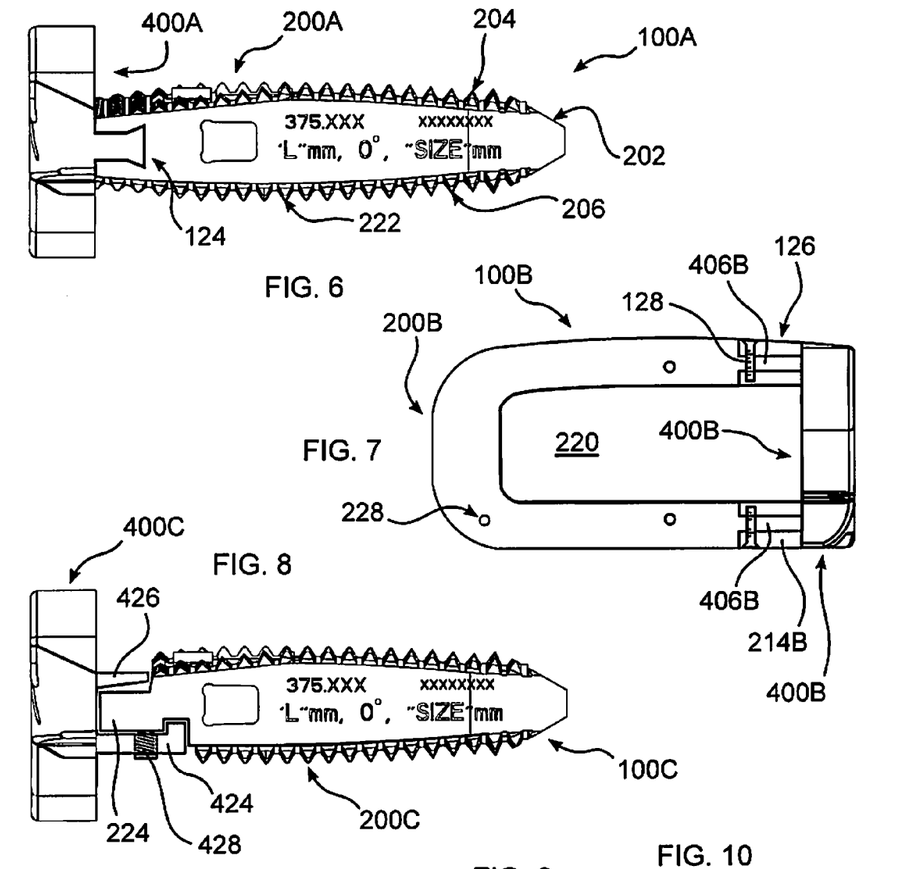
FIG. 6 is a side view of an alternative device of the disclosure, illustrating a dovetail connection between the plate and spacer body.
FIG. 7 is a top view of an alternative device of the disclosure, illustrating an alternative mortise and tenon connection secured by threaded fasteners.
FIG. 8 is a side view of an alternative device of the disclosure, illustrating a biased engagement of projections of the plate and spacer body.

With reference to FIGS. 6-10, any of plate 400A-440D and body 200A-200D are similar to any other embodiment of plate 400 or body 200 described herein, differing in a manner of mutual attachment from that of FIGS. 1-2. In particular, in FIG. 6, device 100A includes a dovetail connection 124 formed between plate 400A and body 200A. In the embodiment shown, plate 400A and body 200A are slid into mutual engagement laterally along an axis transverse to a longitudinal axis of device 100. In variations thereof, a half-dovetail, or any other form of interlocking engagement may be formed, and engagement may occur from top to bottom, also along a transverse axis. In FIG. 6, indicia formed upon device 100 advantageously indicates size information, and may also indicate lot information. Dimensions may include a model designation, length and width of the body or the body and plate combined, as well as a lordotic angle. It may further be seen from FIG. 6 that an upper and or lower surface 204, 206 may be formed with a compound curvature, forming curves which extend longitudinally, as well as laterally.

In FIG. 7, device 100B includes a connection clevis type connection 126 formed between body 200B and plate 400B. This connection is similar to that of FIGS. 1-2, however bars 406B are formed to extend in a direction extending from lower surface 206 to upper surface 204. Clevis 214B is illustrated as being formed from material extending from plate 400B, although it should be understood that clevis 214B could be formed from body 200B, and rod 406B from plate 400. One or more clevis pins 128, which may advantageously be threaded, further secure connection 126. Clevis connection 126 enables pivoting of plate 400B with respect to body 200B, enabling closer conformance to anatomy at the implantation site.

In FIG. 8, device 100C has a connection formed between body 200C and plate 400C by interlocking digits 224 and 424. A biasing element 426 urges body 200C and plate 400C to remain in interlocked configuration, by urging digits 224 and 424 to remain in mutual engagement. A guide 428 may be provided, extending from either plate 400C or body 200C, to facilitate engagement, and or to help prevent unwanted disengagement. Additional fasteners may be used to further secure plate 400C and body 200C together after implantation. Moreover, plate 400C is affixed relative to plate 200C once fasteners 102 are passed through plate 400C and secured in connection with body tissue.

Figures 9, 10:
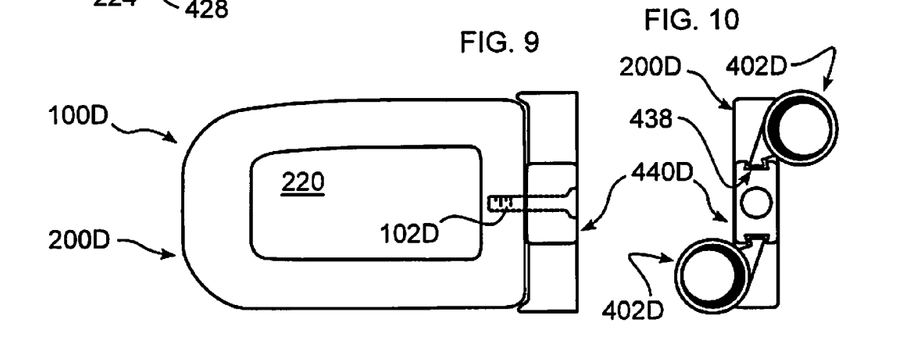
FIG. 9 is a top view of a device including a multipart plate of the disclosure.
FIG. 10 is a front view of the device of FIG. 9, illustrating mating projections between fastener sockets and a base connected to the spacer body.

Referring now to FIGS. 9-10, in device 100D, a dovetail connection 438 is formed between a base 440D and separable sockets 402D. As such, body 200D may be inserted into the body, together with base 440D, through a reduced size incision. Subsequently, one of a plurality of sockets 402D may be passed into the body, and engaged with base 440D, after which a fastener 102 may be inserted through a socket 402D and into body tissue, thereby securing socket 402D to base 440D, and thereby the entirety of the assembled device 100 to the body. Further, base 440D may be pivotally connected to body 200D using a fastener 102D, pin, or other connection which permits rotation of base 440D with respect to body 200D. In this manner, an orientation of body 200D and sockets 402D may be varied to best enable a therapeutic insertion of fasteners 102 through sockets 402D and into the body. In an alternative embodiment, base 440D is affixed to body 200D, or extends as an integral formation of body 200D.

Figures 11, 12, 12A:
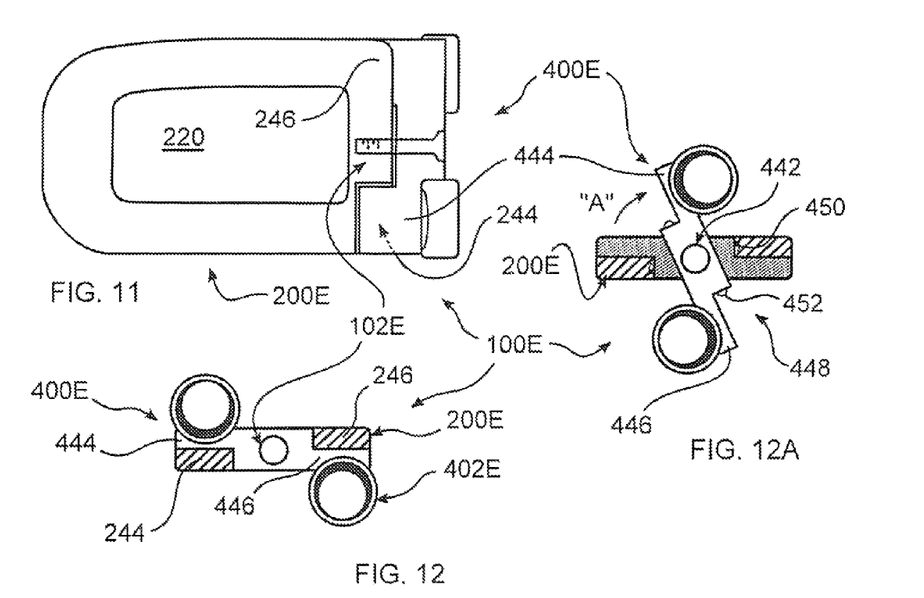
FIG. 11 is a top view of a device of the disclosure including a rotating plate engageable to a spacer body with mating projections.
FIG. 12 is a front view of the device of FIG. 11.
FIG. 12A is a front view of the device of FIG. 11, partially rotated.
Figures 13, 13A:
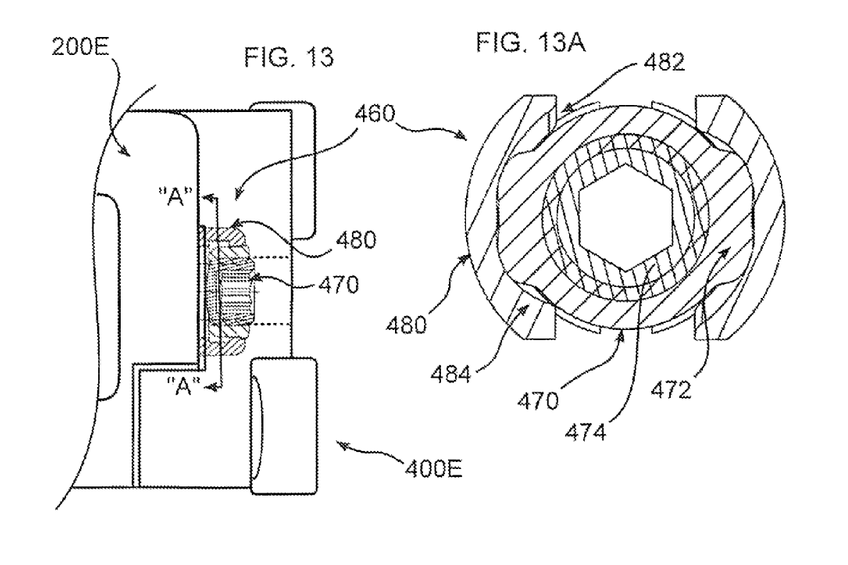
FIG. 13 illustrates an alternative rotating connector of the disclosure.
FIG. 13A is a cross-section of the rotating connector of FIG. 13, taken along line A-A.

In FIGS. 11-13, device 100E includes a plate 400E pivotable about a connection 442 to body 200E. Overlapping panels 444, 446 extending from plate 400E engage mating panels 244, 246 of body 200E when plate 400E is pivoted to be coplanar with body 200E. As panel pairs 244/444, and 246/446 mutually nest, the mated height of body 200E and plate 400E is advantageously no higher than a maximum height of plate 200E, measured from upper surface 204 to lower surface 206, exclusive of sockets 402E, which may extend from panels 444, 446 above and below upper and lower surfaces 204, 206. In this manner, all but sockets 402E may be inserted into a disc space having a uniform height. Further, if therapeutically advantageous, plate 400E may be pivoted, along an arc indicated by arrow "A" in FIG. 12, to position sockets 402E over sturdy body tissue, for example healthy cortical bone, in the event such bone does not lie directly adjacent the intervertebral space into which device 100E is implanted. Alternatively, plate 400E may be implanted in mating engagement with body 200E, which engagement may be indicated and or maintained by a snap fit engagement 448. In the embodiment shown, snap fit engagement 448 includes a mating detent 450 and protrusion 452, which are mutually interlocked when a mating engagement is formed between body 200E and plate 400E. Pivot 102E may include a threaded fastener, pin, post, or other slidable connection.

FIGS. 13-13A illustrate an alternative rotating connection, including a twist-lock connection 460 formed between the body 200E and the plate 400E, one of the plate 400E and body 200E forming a projecting connector portion 470 and the other of the plate and body forming a recessed connector portion 480, the projecting connector portion 470 including a flange 472 and the recessed connector portion 480 including a channel 482 and a stop surface 484. Such interlocking connectors are described in detail in our U.S. Pat. No. 8,034,086 ("the '086 Patent"), issued Oct. 11, 2011, which is incorporated by reference herein. In FIGS. 13-13A, projecting connector portion 470 (cap 200 of the '086 Patent is illustrated, although other cap embodiments disclosed therein may be used) is formed from or connected to plate 400E, and recessed connecting portion (an engaging end portion of coupling body 210 of the '086 Patent) is formed within or connected to body 200E. However, it should be understood that projection connector portion 470 may be associated with body 200E, and recessed connector portion 480 may be associated with plate 400E.

A function of projecting and recessed connector portions 470, 480 is the same as described for their analogs (200, 210) in the '086 Patent. For example, and more particularly, projecting connecting portion 470 is inserted into recessed connecting portion 480, and their associated body 200E and plate 400E are rotated relative to each other, to engage flange 472 within channel 482 until rotation is arrested by stop surface 484. In one embodiment, stop surface 484 prevents overrotation of body 200E and plate 400E, and mating panels 244/444 and 246/446 are not required. In another embodiment, stop surface 484 may not be required, if panels 244/444 and 246/446 are present.

The embodiment of FIGS. 13-13A enables body 200E to be inserted between vertebrae without plate 400E attached. This may facilitate insertion as the overall size of the device is reduced during insertion. For example, this reduced size device comprising body 200E without plate 400E may be inserted through a smaller incision. Additionally, visualization of the insertion site is improved. Subsequently, plate 400E may be engaged and rotated either completely or partially as best indicated by the anatomy at the insertion site. As described in the '086 Patent, a set screw 474 (280 of the '086 Patent) may be used to firmly secure the projecting connecting portion 470 with the recessed connecting portion 480.

Figures 14, 15:
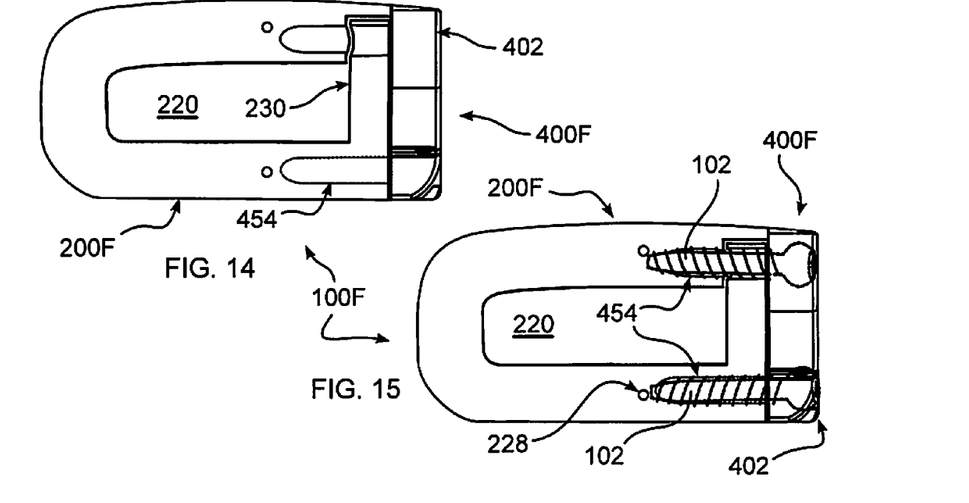
FIG. 14 is a top view of a device of the disclosure, including a spacer body having an engageable extension, and a mating plate.
FIG. 15 is a view of the device of FIG. 14, with fasteners inserted.

FIGS. 14-15 illustrate an alternative device 100F in accordance with the disclosure, including a body 200F having a channel 454 formed to engage a portion of a fastener 102 inserted through socket 402. In this manner, when fastener 102 is connected with body tissue, a lateral displacement of body 200F is resisted by a contact between the portion of fastener 102 nested within channel 454.

A vertical, or superior-inferior displacement is resisted because a similar channel 454, not visible in FIGS. 14-15, is formed on an opposite side of device 100F. When fasteners 102 are positioned in each channel 454, an upwards or downwards movement of body 200F and plate 200F is thus resisted. While, absent other constraints, a relative rotation on one direction of body 200F and plate 400F might be possible, there remains a constraint of body 200F between vertebral endplates, and plate 400F is constrained by fasteners 102 passing through sockets 402 and into body tissue.

A relative anterior-posterior (A/P) displacement between body 200F and plate 400F may be achieved using any of the methods disclosed herein, including for example screw 106 shown in FIGS. 1-2. However, it should be noted that while mortise 214 and tenon 406 may be provided, they are not necessary. Other connection forms which are configured to prevent a relative A/P displacement, including for example the forms shown and described with respect to FIGS. 6-8, which may additionally be used in combination with channels 454.

FIGS. 14-15 additionally illustrate that body 200F may be formed in one or more sections 230 which are flexible or moveable relative to a remainder of body 200F, which sections may be stabilized by the insertion of a fastener 102 within channel 454. By forming body 200F in sections, it becomes possible to pass body 200F into the body through a smaller incision, or to bend body 200F to a smaller profile during insertion, and restore a therapeutically effective shape of body 200F after positioning within the intervertebral space.

With reference to FIGS. 16-21, in some cases, the profile of a plate over an anterior aspect of one or more vertebrae becomes obstructive to anatomy in close proximity. In accordance with an alternative aspect of the disclosure, a device 100G of the disclosure includes an intervertebral spacer body 200G and plate 400G, and which produces an anterior profile which does not protrude from the spinal column. As may be seen in FIG. 18, a vertebra 500A is illustrated, with a device 100G inserted within a space created by removal of portions of the annulus fibrosus 502 and nucleus pulposus 504. It may be seen that plate 400G is sized and dimensioned to advantageously lie entirely within the disc space, and does not extend to contact an anterior aspect of the vertebral body 506.

Figures 16, 17:
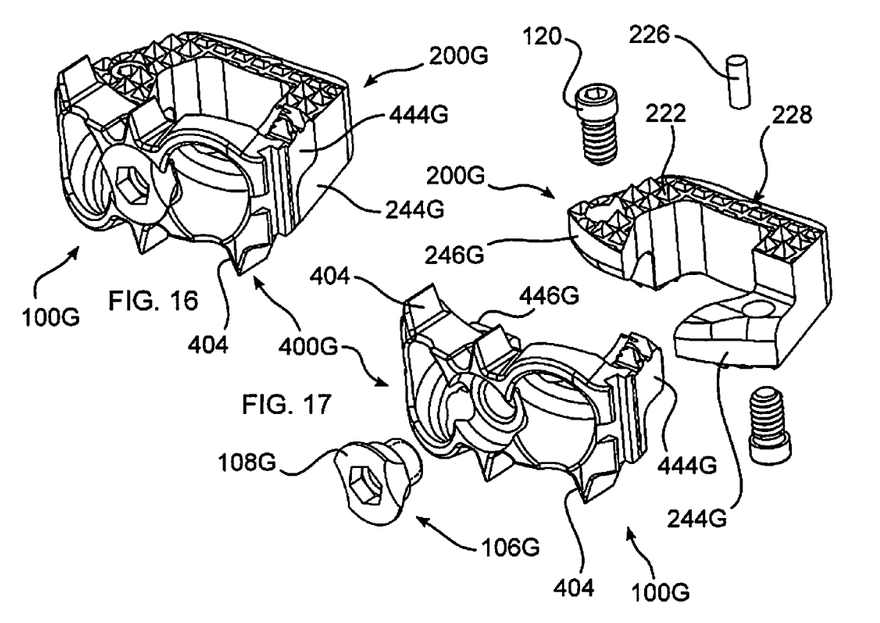
FIG. 16 is a perspective view of a device of the disclosure, including a plate having knife edges, and a spacer body having mateable mirrored projections.
FIG. 17 is an exploded view of the device of FIG. 16.

Body 200G and plate 400G may be mutually connected using any of the structure described herein for other embodiments of the disclosure, as they may be connected using the structure described as follows for the illustrated embodiment of device 100G. More particularly, plate 400G includes a plurality of hook shaped panels 444G, 446G which engaging mating body panels 244G, 246G of body 200G. To help maintain this engagement, fasteners 120, for example machine screws, may be passed through body 200G into plate 400G. Panels 44G, 446G of plate 400G advantageously are provided with teeth 222 on a surface which engages body tissue, whereby a continuous toothed surface is formed between engaged panels 244G and 444G, and engaged panels 246G and 446G. In the illustration, complementary panels 244G, 246G are disposed on opposite upper and lower surfaces 204, 206 of body 200G, as complementary panels 444G, 446G are similarly disposed with respect to plate 400G. In this manner a twisting force between body 200G and plate 400G is resisted in at least one direction by the mutually engaged panels, and in an opposite direction by fasteners 120.

As in other embodiments herein, a blocking cam screw 106G includes a blocking head 108G, provided to prevent backing out of a fastener 102 passed through socket 402. In this embodiment, cam screw 106G is advantageously fastened to plate 400G directly, without engagement to body 200G.

Tortional stabilizers 404 extend from plate 400G, operative thereby to pierce body tissue within the disc space to prevent an unwanted migration of implanted device 100G, and advantageously have the form of axially extending knife edges. In the embodiment shown, two sockets 402 are provided, although a greater or fewer number may be provided, each socket positioned to enable an installed fastener 102 to pass therethrough and into adjacent body tissue at an angle with respect to a plane which bisects upper and lower surfaces 204, 206. Fasteners 102 may, for example, advantageously pass into apophyseal rings of two adjacent vertebrae for increased fixation. As such, a portion of a socket 402 may extend above or below an adjacent upper or lower surface 204, 206. Accordingly, stabilizers 404, are advantageously provided to extend from a side of plate 400G opposite to the portion of socket 402 which extends beyond an adjacent surface, whereby an overall profile height of device 100G may fit within the disc space, and whereby stabilizers 404 and a plurality of teeth 222 may pierce body tissue to stabilize and prevent migration of device 100G from a desired location or region within the body.

Additionally, plate 4000 and or body 200G may be formed with a channel 232G adjacent to aperture 402, sized to receive a portion of fastener 102, which may be particularly advantageous when it is desired to insert fastener 102 at a smaller angle with respect to a plane which bisects upper and lower surfaces 204, 206.

As with other embodiments herein, body 200G is advantageously formed of a polymer, for example PEEK, and plate 400G of titanium, although as explained herein, other materials may be used effectively, depending on forces applied, size, shape, cost, and other factors. Additionally, body 200G, and other spacer bodies of the disclosure, are advantageously shaped to conform to the body tissue being spaced apart. For example, it is advantageous for body 200G to have a curvature upon upper and lower surfaces 204, 206 that is complementary to bony endplates of the vertebrae. A leading taper or chamfer 202 facilitates insertion between body tissue to be separated. An opening within body 200G creates an enclosed volume or chamber 220 into which an optimal quantity of bone graft material 130 may be placed before or after implantation within the body.

By rigidly mounting plate 4000 to body 200G, and sizing and dimensioning device 100G to be fully inserted between adjacent vertebrae, presenting a zero-profile outside of a boundary defined by the vertebral bodies, it is no longer necessary to attach a separate plate to an exterior surface of the vertebral bodes for stabilization.

In an alternative embodiment, illustrated in FIGS. 22-28, a device 100H, is analogous to device 1000 and other devices herein, wherein like reference numerals describe like features, with certain distinctions, some of which are described as follows. Initially, it is noted that device 100H has a different outer shape than device 100G, or other devices of the disclosure, illustrating that devices 100A-100H may be shaped to provide an optimal therapeutic benefit to the patient, as determined by the particular bones between which the device will be implanted. For example, the human spine is organized into lumbar, thoracic, and cervical vertebrae, all sized and shaped differently. To provide beneficial support, it may be advantageous to form devices of the disclosure to overlie cortical bone between vertebrae, while preserving as much soft tissue as possible. For at least this reason, devices of the disclosure are dimensioned to correspond to the anatomy of the bones to be supported, and may be selected prior to, or during a surgical procedure, based on imaging or visualization of the patient's anatomy. Similarly, the size and shape of chamber 220H corresponds to the anatomy of the bones for which device 100H is formed.

As with device 100G, device 100H of the disclosure includes an intervertebral spacer body 200H and plate 400H which produce an anterior profile which does not protrude from the spinal column. As may be seen in FIG. 24, a vertebra 500B is illustrated, with a device 100H inserted within a space created by removal of soft tissue, including portions of the annulus fibrosus and nucleus pulposus. It may be seen that plate 400H is sized and dimensioned to advantageously lie entirely within the disc space, and does not extend to contact an anterior aspect of the vertebral body 506.

Figures 22, 23:
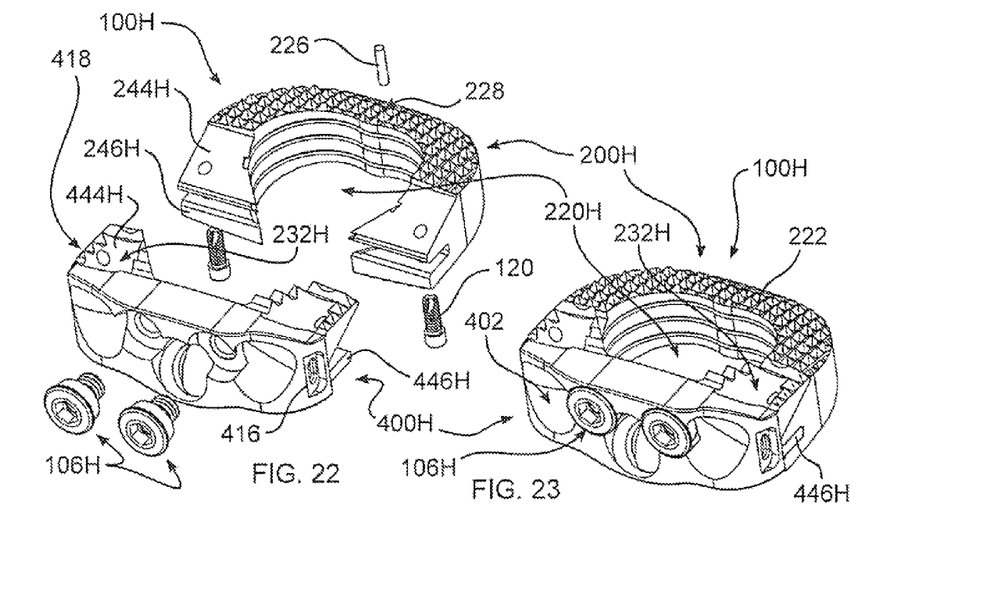
FIG. 22 is an exploded view of an alternative device in accordance with the disclosure, including a mating plate and spacer body.
FIG. 23 is an assembled view of the device of FIG. 22.

Body 200H and plate 400H are mutually connected dovetail or interdigitating panels 444H, 446H which engaging mating body panels 244H, 246H of body 200H. To help maintain an engagement, fasteners 120, for example machine screws, may be passed through body 200H into plate 400H. Panels 444H, 446H of plate 400H advantageously are provided with teeth 222 or edges 418 on a surface which engages body tissue, whereby a continuous tissue engaging surface is formed along a surface 204, 206 of device 100H.

In device 100H, it may be seen that plate 400H forms a portion of the circumference of spacer body 200H, including a portion of chamber 220H. As such, plate 400H imparts greater strength to body 200H, and to the combination of plate 400H and body 200H. Moreover, material of body 200H is not required adjacent to a path of a fastener inserted into the centrally disposed socket 402.

Plate 400H may include blocking screw 106H, which includes a blocking head 108H, provided to prevent backing out of a fastener 102 passed through socket 402. In this embodiment, screw 106H is installed after fastener 102 has been inserted through socket 402; however a cammed retainer, such as blocking cam screw 106H may alternatively be used. Device 100H is provided with three sockets 402 for retaining three fasteners 102. As illustrated, two sockets 402 provide for fasteners to extend into body tissue on a first side of the joint, and one socket 402 provides for a single fastener to extend into body tissue on a second side of the joint. More or fewer sockets 402 may be provided. To balance a retention force, a larger fastener 102 may be used on the side of device 100H which has only a single fastener. A tool engaging recess or structure 416 is formed in plate 400H, which may be grasped by a surgical instrument or tool when maneuvering device 100H into, within, or out of the patient. A tool engaging structure may additionally or alternatively be formed upon body 200H.

Body 200H has a curvature upon upper and lower surfaces 204, 206 that is complementary to bony endplates of the vertebrae, in this embodiment tapering along an A/P dimension as well as a lateral dimension. A leading taper or chamfer 202 facilitates insertion between body tissue to be separated.

By rigidly mounting plate 400H to body 200H, and sizing and dimensioning device 100H to be fully inserted between adjacent vertebrae, presenting a zero-profile outside of a boundary defined by the vertebral bodies, it is no longer necessary to attach a separate plate to an exterior surface of the vertebral bodes for stabilization.

In accordance with all embodiments of the disclosure, procedural steps are eliminated by implanting a unitized spacer body and plate, which provides spacing and alignment, as well as stabilization, eliminating a requirement to shape, position, and fasten a separate plate part. In addition, securing the plate to bone also secures the spacer in an intended location. These features reduce time in the operating room and trauma to the patient, and increase the reliability and effectiveness of the device.

Spacer bodies, plates, fasteners, blocking screws, radiopaque elements, and other structures of the disclosure may be made from biocompatible materials, including polymeric material, such as PEEK (polyether ether ketone), POM (polyoxymethylene), HDPE (high density polyethylene), PPSU (polyphenylsulfone), or acrylic. Biocompatible metals include for example titanium and titanium alloys, tantalum, cobalt-chromium alloy, or stainless steel. Portions of devices of the disclosure, for example plates and bodies, may be mutually joined using an adhesive in addition to, or instead of a threaded fastener, including materials such as a cyanoacrylate. Devices of the disclosure may likewise be bonded to the body using adhesives.

It should be understood that these are examples, and any material that is suitably bio-friendly, and of sufficient mechanical strength and durability may be selected. parts forming the devices of the disclosure, including bodies, plates, and fasteners, may be fabricated using any known or hereinafter developed method, including forging, extrusion, molding, etching, stamping, or casting. Devices ready for implantation are advantageously sterilized and securely packaged.

While the examples provided herein refer to the spinal column, it should be understood that devices of the disclosure may be used to space apart and stabilize other joints of the body, including the finger, wrist, elbow, shoulder, hip, knee, ankle, and toe.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A device for separating and stabilizing first and second adjacent vertebrae together defining an intervertebral space between them, the device comprising:
   a plate comprising a plurality of sockets each configured for retaining a fastener passable through the socket and into the first or second vertebral body, and one or more connecting projections extending from a side of said plate;
   a spacer body having an upper surface and a lower surface sized and dimensioned to be contained within the intervertebral space and the upper surface engageable with the first vertebral body, and the lower surface engageable with the second vertebral body,
   a plurality of teeth projecting from at least one of said upper or lower surface,
   a chamber formed by an opening extending between said upper and lower surfaces, one or more connecting projections of the spacer body mateable with said one or more connecting projections of said plate to thereby securely mutually connect said plate and said spacer body, and
   a fastener extending through the plate for engaging a vertebral body, wherein the fastener comprises a head and a body that extends along a straight longitudinal axis,
   wherein one or more connecting projections of the plate are configured with an upper surface and a lower surface and extend rearward and the upper surface is configured and dimensioned to contact the first vertebral body
   wherein the upper surface of the spacer body is defined by a plane, and a portion of the head of the fastener extends above the plane of the upper surface.

2. The device of claim 1, wherein the plate is sized and dimensioned to be contained within the intervertebral space.

3. The device of claim 1, wherein the upper surface of the connecting projection of said plate includes a plurality of teeth or an edge configured to engage a vertebral body.

4. The device of claim 1, wherein the fastener is passed through the socket and into the first or second vertebral body and lies partially within a channel formed in said upper or lower surface.

5. The device of claim 4, wherein no portion of the fastener that is passed through the socket and into the first or second vertebral body extends outside the intervertebral space.

6. The device of claim 1, further including a blocking cam screw configured to block movement of the fastener passed through one of said sockets in a direction of passing out of one of said sockets.

7. The device of claim 6, said blocking cam screw including a blocking head having a cam profile including a fastener access portion and a fastener blocking portion.

8. The device of claim 1, said plate further including at least one edge extending therefrom and configured to enter a vertebral body when said device is implanted between adjacent vertebrae.

9. The device of claim 8, wherein said edge is aligned in an anterior-posterior direction when said device is implanted, said edge is thereby configured to resist a lateral movement of said device.

10. The device of claim 1, wherein said chamber is configured to admit the introduction of bone growth material, and to permit the growth of bone from the adjacent vertebrae, into said chamber and through said device.

11. The device of claim 1, said device configured to be inserted from an anterior approach to the intervertebral space, after the removal of body tissue from the intervertebral space.

12. The device of claim 1, wherein said plate and body connecting projections are mutually secured in engagement by at least one threaded fastener.

13. The device of claim 1, wherein said plate and body connecting projections are maintained in engagement by a threaded fastener passable from said plate into said body.

14. The device of claim 1, wherein said device is configured to be inserted from a lateral approach to the intervertebral space, after the removal of body tissue from the intervertebral space.

15. A device for separating and stabilizing first and second adjacent vertebrae together defining an intervertebral space between them, the device comprising:
   a plate comprising a plurality of sockets each configured for retaining a fastener passable through the socket and into the first or second vertebral body, and one or more connecting projections extending from a side of said plate;

a spacer body having an upper surface and a lower surface sized and dimensioned to be contained within the intervertebral space and the upper surface engageable with the first vertebral body, and the lower surface engageable with the second vertebral body, a plurality of teeth projecting from at least one of said upper or lower surface, a chamber formed by an opening extending between said upper and lower surfaces, one or more connecting projections of the spacer body mateable with said one or more connecting projections of said plate to thereby securely mutually connect said plate and said spacer body, and a fastener extending through the plate for engaging a vertebral body, wherein the fastener comprises a head and a body that extends along a straight longitudinal axis, wherein one or more connecting projections of the plate are configured with an upper surface and a lower surface and extend rearward and the upper surface is configured and dimensioned to contact the first vertebral body wherein the upper surface of the spacer body is defined by a plane, and a portion of the head of the fastener extends above the plane of the upper surface.

16. A device for separating and stabilizing first and second adjacent vertebrae together defining an intervertebral space between them, the device comprising:

a plate comprising a plurality of sockets each configured for retaining a fastener passable through the socket and into the first or second vertebral body, and one or more connecting projections extending from a side of said plate;

a spacer body having an upper surface and a lower surface sized and dimensioned to be contained within the intervertebral space and the upper surface engageable with the first vertebral body, and the lower surface engageable with the second vertebral body, a plurality of teeth projecting from at least one of said upper or lower surface, a chamber formed by an opening extending between said upper and lower surfaces, and one or more connecting projections of the spacer body mateable with said one or more connecting projections of said plate to thereby securely mutually connect said plate and said spacer body, and a fastener extending through the plate for engaging a vertebral body, wherein the fastener comprises a head and a body that extends along a straight longitudinal axis, wherein one or more connecting projections of the plate are configured with an upper surface and a lower surface and extend rearward and the upper surface is configured and dimensioned to contact the first vertebral body wherein the spacer body is configured with no boreholes or partial boreholes for receiving the fastener.

* * * * *